ized Patent [19]

United States Patent [19]
Gordon et al.

[11] Patent Number: 4,672,075
[45] Date of Patent: Jun. 9, 1987

[54] 7-OXABICYCLO(2.2.1)HEPTANE HYDROXAMIC ACID DERIVATIVES USEFUL AS ANTIINFLAMMATORY, ANTIASTHMA AND ANTIPSORIATIC AGENTS

[75] Inventors: Eric M. Gordon, Pennington; Ravi K. Varma, Belle Mead, both of N.J.

[73] Assignee: E. R. Squibb & Sons, Princeton, N.J.

[21] Appl. No.: 900,565

[22] Filed: Aug. 26, 1986

[51] Int. Cl.$^4$ .................. A61K 31/34; A61K 31/557; C07D 307/00
[52] U.S. Cl. ...................................... 514/469; 549/463
[58] Field of Search .................... 549/463; 514/469

[56] References Cited
U.S. PATENT DOCUMENTS

| | | | |
|---|---|---|---|
| 4,143,054 | 3/1979 | Sprague | 549/463 |
| 4,228,180 | 10/1980 | Sprague | 549/463 |
| 4,254,044 | 3/1981 | Sprague | 549/463 |
| 4,497,827 | 2/1985 | Nelson | 514/381 |
| 4,582,854 | 4/1986 | Hall et al. | 549/463 |
| 4,604,407 | 8/1986 | Haslanger et al. | 514/575 |

FOREIGN PATENT DOCUMENTS 0083204 7/1983 European Pat. Off. .

Primary Examiner—Henry R. Jiles
Assistant Examiner—Bernard I. Dentz
Attorney, Agent, or Firm—Lawrence S. Levinson; Theodore R. Furman, Jr.

[57] ABSTRACT

7-Oxabicyclo(2.2.1)heptane hydroxamic acid derivatives are disclosed having the general formula

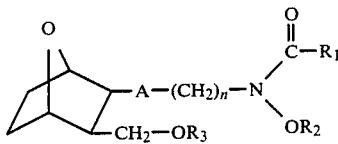

wherein $R_1$ is hydrogen, lower alkyl, aryl, aralkyl or alkenyl; $R_2$ is hydrogen, lower alkyl, alkanoyl or aroyl; $R_3$ is lower alkyl, alkenyl or alkynyl; A is —CH$_2$—CH=CH— or a single bond; and n is an integer from 0 to 9, with the proviso that when A is a single bond, n is an integer from 1 to 9; and including all stereoisomers and pharmaceutically acceptable salts thereof.

These new compounds have been found to simultaneously inhibit the arachidonic acid enzymes cyclooxygenase and 5-lipoxygenase and are therefore useful as antiinflammatory, antiasthma and antipsoriatic agents.

12 Claims, No Drawings

7-OXABICYCLO(2.2.1)HEPTANE HYDROXAMIC ACID DERIVATIVES USEFUL AS ANTIINFLAMMATORY, ANTIASTHMA AND ANTIPSORIATIC AGENTS

FIELD OF THE INVENTION

The present invention relates to 7-oxabicyclo(2.2.1-)heptane hydroxamic acid derivatives and more particularly concerns such derivatives which simultaneously inhibit the enzymes arachidonic acid cyclooxygenase and arachidonic acid 5-lipoxygenase and as such are useful, for example, as antiinflammatory, antiasthma and antipsoriatic agents.

BACKGROUND OF THE INVENTION

In a copending application (filed concurrently herewith), entitled "7-OXABICYCLO(2.2.1)HEPTANE ANALOGS", compounds of the formula

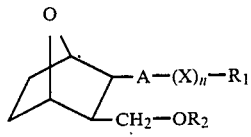

are disclosed wherein $R_1$ is lower alkyl, alkenyl, substituted alkenyl or alkynyl; $R_2$ is lower alkyl, alkenyl or alkynyl; A is —$CH_2$—CH=CH— or a single bond; X is $CH_2$, $CH(CH_3)$ or $C(CH_3)_2$; and n is an integer from 0 to 9, with the proviso that when A is a single bond, n is an integer from 1 to 9. These compounds have been found to be inhibitors of the enzyme arachidonic acid cyclooxygenase and as such are useful as antiinflammatory agents in that they prevent the formation of various prostaglandins.

In European Patent Application No. 823068689 to Wakatsuka 2-amino-4-phenylthio-phenol compounds and their analogs are disclosed having utility as inhibitors of both 5-lipoxygenase and cyclooxygenase. New compounds effective as "dual inhibitors", i.e. inhibitors of both arachidonic acid enzymes 5-lipoxygenase and cyclooxygenase, would be a useful addition to the art.

SUMMARY OF THE INVENTION

In accordance with the present invention new 7-oxabicyclo(2.2.1)heptane hydroxamic acid derivatives useful as inhibitors of arachidonic acid 5-lipoxygenase and arachidonic acid cyclooxygenase are provided. These new compounds have the general formula

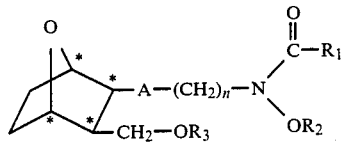

wherein $R_1$ is hydrogen, lower alkyl, aryl, aralkyl or alkenyl; $R_2$ is hydrogen, lower alkyl, alkanoyl or aroyl; $R_3$ is lower alkyl, alkenyl or alkynyl; A is —$CH_2$—CH=CH— or single bond; and n is an integer from 0 to 9, with the proviso that when A is a single bond, n is an integer from 1 to 9; and including all stereoisomers and pharmaceutically acceptable salts thereof.

DETAILED DESCRIPTION OF THE INVENTION

The hydroxamic acid derivatives of the present invention may form salts with alkali metals, such as lithium, sodium or potassium. In addition, the compounds of formula I will form salts with dicyclohexylamine or other amines as well as with tris(hydroxymethyl-)aminomethane, glucamine a amines as set out in U.S. Pat. No. 4,294,759.

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an aralkyl substituent, a haloaryl substituent, a cycloalkyl substituent, an alkylcycloalkyl substituent, hydroxy, an alkylamino or dialkylamino substituent, an alkanoylamino substituent, an arylcarbonylamino substituent, a nitro substituent, a cyano substituent, a thiol substituent or an alkylthio substituent.

The term "cycloalkyl" employed herein by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, which groups are substituted with the same, or a different cycloalkyl.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substitutent on either the phenyl or naphthyl may be 1 or 2 lower alkyl groups, 1 or 2 halogens (Cl, Br or F), 1 or 2 lower alkoxy groups, 1 or 2 hydroxyl groups, 1 or 2 alkylamino or dialkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

The term "aralkyl", "aryl-alkyl" or "aryl-lower alkyl" as used herein refers to lower alkyl groups as discussed above having an aryl substituent, such as benzyl.

The term "lower alkenyl" or "alkenyl" as employed herein by itself or as part of another group includes an unsaturated hydrocarbon group having from 2 to 8 carbons and a single carbon-carbon double bond, such as ethenyl, 1-propenyl, 2-propenyl, 1-butenyl, 2-butenyl, 3-butenyl and the like.

The term "lower alkynyl" or "alkynyl" as employed herein by itself or as part of another group includes an unsaturated hydrocarbon group having from 3 to 8 carbons and a single carbon-carbon triple bond, such as 1-propynyl, 2-propynyl, 1-butynyl, 2-butynyl, 3-butynyl and the like.

The term "alkanoyl" as used herein by itself or as part of another group refers to an alkyl carbonyl or alkenyl carbonyl group.

The term "aroyl" as used herein by itself or as part of another group refers to an aryl carbonyl group.

The term "halogen" or "halo" as used herein refers to chlorine, bromine, fluorine or iodine with chlorine being preferred.

Preferred are those compounds of the invention wherein $R_1$ is methyl, $R_2$ is hydrogen, $R_3$ is n-hexyl, A is $CH_2-CH=CH$ and n=3 or 4.

The various compounds of the invention may be prepared as described below.

To make the compounds of formula I, a carboxylic acid of the formula

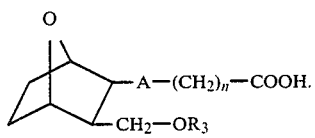
II

The preparation of which has been described in U.S. Pat. No. 4,582,854, is reduced with lithium aluminum hydride in the presence of a dry organic solvent, e.g. tetrahydrofuran or ether, to the alcohol

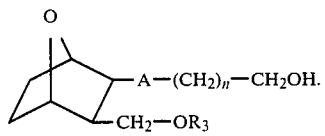
III

The reaction of the alcohol III with a complex prepared from N-bromosuccinimide and triphenylphosphine at a temperature within the range of from about 0° C. to about 25° C. affords a bromide of the formula

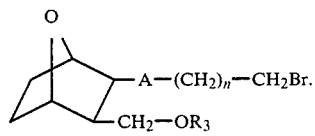
IV

The bromide IV can be reacted with a hydroxylamine in which the oxygen is protected, e.g. O-tetrahydropyranyloxy hydroxyl amine in the presence of a solvent, e.g. dimethylformamide, and a base, e.g. sodium bicarbonate, at a temperature within the range of from about 25° C. to about 70° C. to produce

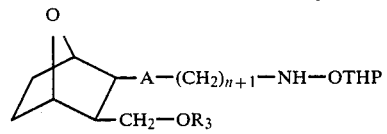
V in which the tetrahydropyranyl (THP) "O"-protecting group" appears as shown. Amine V can thereafter be reacted with a carboxylic acid chloride of the formula

$R_1-COCl$    VI (wherein $R_1$ is the desired alkyl or aryl group) in the presence of a base, e.g. aqueous sodium hydroxide and a solvent such as tetrahydrofuran to afford the "O-protected" hydroxamic acid

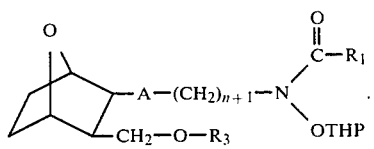
VII

Compound VII, where $R_1=H$, can be prepared by the reaction of V with acetic formic anhydride preferably in the presence of a base such as triethylamine.

Compound VII is thereafter "de-protected", such as by treatment with pyridinium-paratoluene sulfonate in methanol or dilute hydrochloric acid in methanol, to remove the THP group and provide the compounds of the present invention.

Alternatively, the alcohols of formula III can be prepared by the Wittig reaction of an aldehyde of the formula

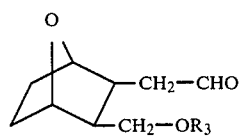
VIII with the phosphonium salts of the formula

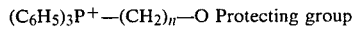
$(C_6H_5)_3P^+-(CH_2)_n-O$ Protecting group    IX in the presence of bases to afford

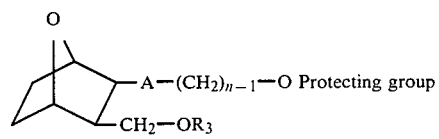
X wherein the protecting group can be THP, t-butyl dimethyl silyl, or the like. Compound X can thereafter be "deprotected", e.g. by treatment with tetrabutylammonium fluoride or dilute acetic acid (in the case of t-butyl dimethyl silyl) or pyridinium paratoluene sulfonate or dilute hydrochloric acid in methanol (in the case of THP) to produce the alcohols III.

The aldehyde VIII may be substituted by the hemiacetal XI

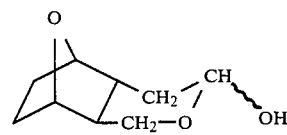
XI for reaction with the phosphonium salt IX and afford alcohols of the formula XII

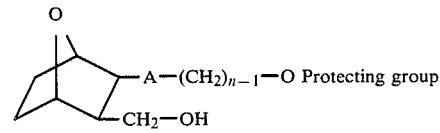
XII

Alcohols of formula XII can be reacted with mesylates or tosylates of formula

$R_3-X$    XIII where X=mesyloxy or p-toluene sulfonyloxy in the presence of an inorganic base like potassium hydroxide in an organic solvent like xylene at temperatures within the range of 100° C. to 150° C. to afford ethers of the formula X which can thereafter be "deprotected" as described before to produce alcohols III.

Another alternative includes converting the alcohols III into tosylates or mesylates, instead of the bromides IV, for reaction with the O-tetrahydropyranyloxy hydroxylamine.

The compounds of this invention have four centers of asymmetry as indicated by the asterisks in formula I. However, it will be apparent that each of the formulae set out above which do not include asterisks still represent all the possible stereoisomers thereof. All of the various stereoisomeric forms are within the scope of the present invention.

The various stereoisomeric forms of the compounds of the invention, namely, cis-endo, cis-exo and all trans forms and stereoisomeric pairs may be prepared as shown in the working Examples which follow and by employing starting materials and following the procedures as outlined in U.S. Pat. No. 4,582,854. Examples of such stereoisomers are set out below.

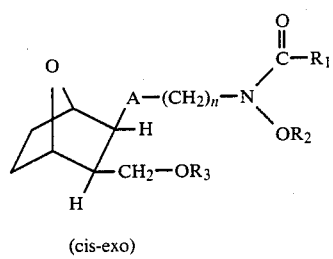

(cis-exo) Ia

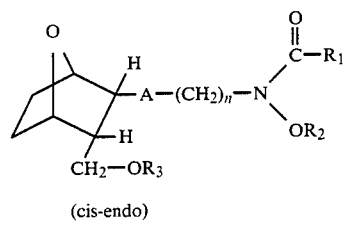

(cis-endo) Ib

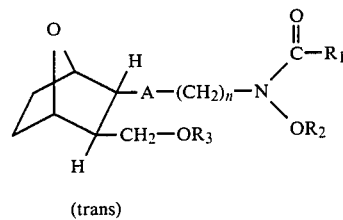

(trans) Ic

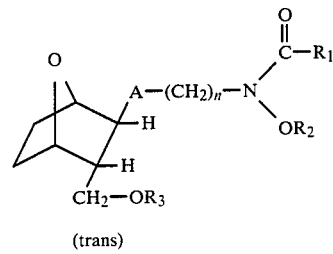

(trans) Id

The nucleus in each of the compounds of the invention is depicted as

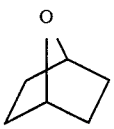

for matter of convenience; it will also be appreciated that the nucleus in the compounds of the invention may be depicted as

The compounds of the invention are inhibitors of the arachidonic acid enzymes 5-lipoxygenase and cyclooxygenase and prevent formation of certain leukotriene and prostaglandins. The administration of compounds of this invention to humans or animals provides a method for treating allergy of a reagin or non-reagin nature. Asthma and psoriasis are preferably treated but any allergy or inflammation wherein leukotrienes or prostaglandins are thought to be involved as pharmacological mediators can be treated. For example, the compounds of this invention can be used for treatment of such conditions as allergic rhinitis, food allergy and urticaria, as well as asthma and psoriasis.

An effective but essentially non-toxic quantity of the compound is employed in treatment.

The compounds of the invention can be administered parenterally, orally or topically to various mammalian species known to be subject to such maladies, e.g., humans, cattle, horses, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension, lotion, cream or ointment containing about 5 to about 5000 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following examples represent preferred embodiments of the present invention.

EXAMPLE 1

[1R-[1α,2β(3Z),3β,4α]]-N-[5-[3-[(Hexyloxy)-methyl]-7-oxabicyclo[2.2.1]hept-2-yl]-3-pentenyl]-N-hydroxyacetamide A. 3-Iodo-1-tetrahydro-2-pyranyloxy propane A solution of 3-iodopropanol (15 g, 80.65 mole), dihydropyran (14.7 ml, 161.29 mole) and pyridium p-toluenesulfonate (500 g, 2.0 mole) in 100 ml of dry dichloromethane was stirred at room temperature under an atmosphere of nitrogen for 2.5 hours. The resulting mixture was diluted with dichloromethane (150 ml), washed with water and a saturated sodium bicarbonate solution, dried over anhydrous magnesium sulfate and evaporated in vacuo. The residue was flash chromatographed on a silica gel to give 20.43 g of the title A compound as an oil.

B. 3-Tetrahydropyranyloxypropyl triphenyl phosphonium iodide

A solution of 3-iodo-1-tetrahydro-2-pyranyloxy propane (20.43 g, 75.63 mmole), and triphenylphosphine (19.84 g, 75.63 mmole) in 150 ml of dry benzene was refluxed under an atmosphere of nitrogen for 24 hours. The solvent was evaporated in vacuo to give a sticky gum. This was rinsed with acetonitrile (80 ml) when a white solid precipitated out. The solid was filtered and dried over phosphorous pentoxide at 60° C. in vacuo for 20 hours to give 32.8 g of the title B compound.

C. 1R-[1α,2β(2Z),3β,4α]-5-[[3(Hydroxymethyl)]-7-oxabicyclo(2.2.1)hept-2-yl]-tetrahydro-2-pyranyloxy-pent-2-ene To a chilled and stirred slurry of 3-tetrahydro-2-pyranyloxy triphenyl phosphonium iodide (4.224 g, 9 mmole) in 40 ml of dry tetrahydrofuran was added dropwise potassium-t-amylate (4.03 ml, 1.7M in toluene) over five minutes under nitrogen. The orange solution was stirred at −20° for 2 hours and then a solution of 1R-[4aR-(4aα,5α,8α,8aα)]octahydro-5,8-epoxy-(1H)-benzopyrane-3-ol (510 mg, 3 mmole) in 10 ml of dry tetrahydrofuran was added dropwise. The solution was gradually warmed up to room temperature, stirred for 18 hours and quenched with acetaldehyde (1.5 ml). After stirring at room temperature for another 30 minutes, the mixture was diluted with 30 ml of a saturated sodium bicarbonate solution and extracted three times with ethyl ether. The combined ether extracts were washed with brine, dried over anhydrous magnesium sulfate and evaporated in vacuo. The residue was flash-chromatographed on a silica gel to give 810 g of the title C compound as an oil.

D. 1R-[1α,2β(2Z),3β,4α]-5-[[3(Hexyloxy)methyl]-7-oxabicyclo(2.2.1)hept-2-yl]tetrahydro-2-pyranyloxy-pent-2-ene Powdered potassium hydroxide (900 mg, 16 mmole) in 80 ml of dry xylene was refluxed under stirring in an atmosphere of nitrogen and 35–40 ml of xylene was removed by distillation. To this was added dropwise a solution of the alcohol of step C (400 mg, 1.35 mmole) and n-hexylmesylate (1.216 g, 6.75 mmole) in 25 ml of dry xylene. The mixture was refluxed for one hour and was then cooled. Water (25 ml) was added and the solution was extracted three times with ethyl ether. The combined ether extracts were washed with brine, dried over anhydrous magnesium sulfate and evaporated in vacuo. The residue was flash chromatographed on a silica gel column to give 455 mg of title D compound as an oil.

E. 1R-[1α,2β(2Z),3β,4α]-5-[[3(Hexyloxy)methyl]-7-oxabicyclo(2.2.1)hept-2-yl]pent-2-enol A solution of the ether of step D (125 mg, 0.328 mmole) and pyridium p-toluenesulfonate (91 mg, 0.361 mmole) in 5 ml of methanol was stirred at 70° (oil bath temperature) under an atmosphere of nitrogen for 1.5 hours. The methanol was mostly removed in vacuo, the residue diluted with 15 ml of water and extracted three times with ethyl ether. The combined ether extracts were washed with brine, dried over anhydrous magnesium sulfate and evaporated in vacuo. The residue was flash chromatographed on a silica gel column to give 85 mg of the title E compound.

F. 1R-[1α,2β(2Z),3β,4α]-5-[[3-(Hexyloxy)methyl]-7-oxabicyclo(2.2.1)hept-2-yl]-bromo-2-pentene N-Bromosuccinimide (356 mg, 2 mmole), triphenylphosphine (524.6 mg, 2 mmole) and dry Celite (dried at 100° in vacuo overnight) were mixed in benzene (15 ml) at 0° under an atmosphere of nitrogen and then stirred at room temperature for 1.5 hours. A solution of the alcohol of step E (296.5 mg, 1 mmole) in dichloromethane (5.0 ml) was added. After stirring for 18 hours, the mixture was filtered through a bed of Celite and washed with a small amount of dichloromethane. The filtrate and washings were dried over anhydrous magnesium sulfate and evaporated in vacuo. The residue was chromatographed on a silica gel column to give 340 mg of the title F compound as an oil.

G. 1R-[1α,2β(2Z),3β,4α]-5-[[3(Hexyloxy)methyl]-7-oxabicyclo(2.2.1)hept-2-yl]-[N(tetrahydro-2-pyranyloxy)amino]-pent-2-ene A mixture of the bromide of step F (450 mg, 1.25 mmole), O-tetrahydropyranyloxy hydroxylamine (293 mg, 2.5 mmole) and anhydrous sodium bicarbonate (1.05 g, 12.5 mmole) in 7 ml of dry HMPA was stirred at 70° C. (oil bath temperature) under an atmosphere of nitrogen for 18 hours. The mixture was then cooled to room temperature, diluted with water (20 ml) and extracted three times with ethyl ether. The ether extracts were combined and washed several times with water, dried over anhydrous magnesium sulfate and evaporated in vacuo. The residue was chromatographed on a silica gel column to give 400 mg of the title G compound as an oil.

H. 1R-[1α,2β(3Z),3β,4α]-N-[5-[3-(Hexyloxy)methyl]-7-oxabicyclo(2.2.1)hept-2-yl]-3-pentenyl-N-(tetrahydro-2-pyranyloxy) acetamide A mixture of the compound of step G (395.6 mg, 1 mmole) and 1.0N sodium hydroxide (20 ml, 20 mmole) in 10 ml of tetrahydrofuran was stirred vigorously at ~0° C. under an atmosphere of nitrogen. A solution of acetyl chloride (0.285 ml, 4 mmole) in 3 ml of tetrahydrofuran was then added dropwise. The mixture was stirred at ~0° for five hours and extracted three times with ethyl ether. The combined ether extracts were washed with brine, dried over anhydrous magnesium sulfate, filtered and evaporated in vacuo to give 415 mg of slightly impure the title H compound, as an oil.

I. 1R-[1α,2β(3Z),3β,4α]-N-[5-[3-(Hexyloxy)methyl]-7-oxabicyclo[2.2.1hept-2-yl]-3-pentenyl]-N-hydroxyacetamide A solution of the compound of step H (415 mg, 0.948 mmole) and pyridium p-toluenesulfonate (400 mg, 1.59 mmole) in 20 ml of dry methanol was stirred at 75° C. (oil bath temperature) under an atmosphere of nitrogen for five hours. The solvent was then evaporated in vacuo. The residue was diluted with water (20 ml) and extracted three times with ethyl ether. The combined ether extracts were washed with brine, dried over anhydrous magnesium sulfate and evaporated in vacuo. The residue was chromatographed on a silica gel to give 245 mg of the title compound as an oil.

EXAMPLE 2

[1R-[1α,2β(4Z),3β,4α]]-N-[6-[3-[(Hexyloxy)methyl]-7-oxabicyclo[2.2.1]hept-2-yl]-4-hexenyl]-N-hydroxyacetamide

A.

1R-[1α,2β(Z),3β,4α]-6-[3-[(Hydroxy)methyl]-7-oxabicyclo(2.2.1)hept-2-yl]-4-hexenoic acid A slurry of 3-carboxypropyltriphenylphosphonium iodide (41.13 g, 0.086 mole) and [4aR(4aα,5α,8α,8aα)]-Octahydro-5,8-epoxy-(1H)-benzypyrano-3-ol (10 g, 0.059 mole) in dry toluene (236 ml) was chilled to ~0° C. under nitrogen and treated dropwise with a solution of 1.74M potassium t-amylate in toluene (97.1 ml, 0.169 mole) over a period of ninety minutes. The mixture was then stirred at room temperature for twenty hours, chilled to ~0° C. and treated slowly with glacial acetic acid (9.5 ml) in toluene (11.8 ml) in the course of thirty minutes. The thick suspension was treated with water (177 ml) and brought to a pH of about 1.5 with concentrated hydrochloric acid (12 ml). The mixture was diluted with ethyl acetate (177 ml), treated with sodium chloride (41.3 g) and stirred vigorously for fifteen minutes. The resultant precipitates were removed by filtration, washing the solids twice with ethyl acetate. The toluene-ethyl acetate layer was separated and the aqueous layer extracted twice with ethyl acetate. The combined organic extracts were dried over anhydrous magnesium sulfate and concentrated in vacuo to a thick oil. This oil was stirred vigorously with 5% potassium carbonate (177 ml) for 30 minutes, filtered and the resultant solid washed thoroughly with water (100 ml). The aqueous filtrate was extracted with ethyl ether:toluene (1:1; 5 times), chilled in an ice bath and treated slowly with concentrated hydrochloric acid to pH 2.5. The aqueous layer was extracted three times with ethyl acetate and the combined extracts were dried over anhydrous magnesium sulfate, filtered and concentrated in vacuo to give 15.2 g of the title A compound as a thick oil.

B.

1R[1α,2β(Z),3β,4α]-6-[3-[(Hydroxy)methyl]-7-oxabicyclo(2.2.1)hept-2-yl]-4-hexenoic acid, methyl ester A solution of the title A compound (15.2 g, 0.059 mole) in dry methanol (78 ml) was stirred vigorously with crushed amberlyst-15 resin (7.70 g) at room temperature for two days. The mixture was diluted with ether (80 ml) and filtered through a Celite pad, washing the pad thoroughly with ether. The combined filtrate and washings were concentrated in vacuo, the resultant oil was dissolved in ether (150 ml) and washed with a 5% sodium bicarbonate solution (25 ml), water (20 ml) and brine (20 ml). The organic phase was dried over anhydrous magnesium sulfate, filtered and concentrated in vacuo to a thick oil which contained the title compound as the major component and small amounts of three less polar components. This product mixture was chromatographed on a silica gel column to give 8.88 g of the title B compound as an oil.

C.

1R-[1α,2β(Z),3β,4α]-6-[3-[(Hexyloxy)methyl]-7-oxabicyclo(2.2.1)hept-2-yl]-4-hexenoic acid, methyl ester A stirred suspension of crushed potassium hydroxide (18.4 g) in dry xylene (700 ml) was brought to reflux under nitrogen and 180 ml of xylene was removed by distillation. The mixture was cooled and a solution of the title B compound (9.2 g, 0.036 mole) and n-hexylmesylate (33 g, 0.18 mole) in dry xylene (60 ml) was added. The mixture was gently refluxed, azeotroping off xylene (~180 ml) over a period of one hour, cooled and treated with a solution of potassium hydroxide (18.5 g, 0.33 mole) in water (220 ml). The solution was refluxed under vigorous stirring for 1.5 hours, cooled, diluted with water (450 ml) and extracted with ether (2.0 liters). The aqueous layer was acidified with concentrated hydrochloric acid (50 ml), extracted three times with ether, and the combined organic extracts washed with brine (450 ml), dried over anhydrous magnesium sulfate, filtered and evaporated in vacuo to give the acid corresponding to the title compound as a thick oil (10.4 g). The crude acid was dissolved in ether (150 ml), cooled down to 0° C. and treated with excess diazomethane in ether. The yellow solution was allowed to stand at 0° C. for thirty minutes, at room temperature for one hour and the excess diazomethane blown off with a stream of nitrogen. The resulting solution was evaporated in vacuo and the residual oil chromatographed on a silica gel column to give 10.05 g of the title C compound as a homogeneous oil.

1R[1α,2β(Z),3β,4α]-6-[3-[(Hexyloxy)methyl-7-oxabicyclo(2.2.1)hept-2-yl]-4-hexenol A solution of the title C compound (5 g, 0.015 mole) in dry tetrahydrofuran (25 ml) was added under nitrogen to a cooled (~0° C.) suspension of lithium aluminum hydride (936.2 mg, 0.025 mole) in dry tetrahydrofuran (115 ml). The mixture was stirred at ~0° C. for thirty minutes, at room temperature for 2.5 hours and quenched by the subsequent addition of water (1.0 ml), 10% sodium hydroxide (1.5 ml) and water (3.0 ml). The slurry was stirred for thirty minutes, diluted with ether (100 ml) and the supernatant solution was decanted, washing the precipitates thrice with ether (225 ml). The combined organic extracts were dried over anhydrous magnesium sulfate, filtered and evaporated to dryness to give an oil (5.04 g) which contained the title compound as the major component and traces of three more polar components. The crude product was chromatographed on a silica gel to give 353 g of the title D compound as a homogeneous oil.

E.

1R-[1α,2β(Z),3β,4α]-6-[3-(Hexyloxy)methyl]-7-oxabicyclo(2.2.1)hept-2-yl]bromo-4-hexene A mixture of 99% triphenylphosphine (5.44 g, 20.5 mmole), N-bromosuccinimide (3.67 g, 20.6 mmole) and Celite (11.6 g) was stirred at ~0° C. in a mixture of dry benzene (116 ml) and dry dichloromethane (29 ml) under nitrogen for ten minutes and at room temperature for one hour. A solution of the alcohol of step D (2.89 g, 9.3 mmole) in dry dichloromethane (50 ml) was added to the resulting complex and the stirring continued at room temperature for 24 hours. The mixture was diluted with dichloromethane (50 ml), stirred and filtered, washing the solids with more dichloromethane (300 ml). The filtrate and washings were combined and evaporated to dryness and the residual oil partitioned twice between water (150 ml) and dichloromethane (300 ml). The organic phase was dried over anhydrous magnesium sulfate, filtered and evaporated to dryness to give an oil containing traces of triphenylphosphine and a slightly more polar component. The crude product was chromatographed on a silica gel column to give 3.10 g of the title E compound as a homogeneous oil.

F. 1R-[1α,2β(Z),3β,4α]-6-[3-(Hexyloxy)methyl]-7-oxabicyclo(2.2.1)hept-2-yl-N[(tetrahydro-2-pyranyloxy)amino]-4-hexene A mixture of the title E compound (800 mg, 2.14 mmole), 0-tetrahydropyranyloxy hydroxylamine (501.6 mg, 4.28 mmole, 2 eq.) and sodium bicarbonate (1.8 g, 21.4 mmole) in dry HMPA (10.4 ml) was heated at 70° (oil-bath) under nitrogen for 6.5 hours. The mixture was then cooled, diluted with water (50 ml) and extracted three times with ether. The combined organic extracts were washed with brine (40 ml), dried over anhydrous magnesium sulfate, filtered and evaporated to dryness. The residual oil was chromatographed on a silica gel column to give 838.9 mg of the title F compound as a homogeneous oil.

G. [1R-[1α,2β(Z),3β,4α]]-N-[6-[3-[(Hexyloxy)methyl]-7-oxabicyclo(2.2.1)hept-2-yl]-4-hexenyl]-N-(tetrahydro-2-pyranyloxy) acetamide A solution of the title F compound (833.6 mg, 2.04 mmole) in 1N sodium hydroxide (40.7 ml, 20 eq.) and tetrahydrofuran (20.4 ml) was stirred vigorously at ~0° C. and treated dropwise with a solution of acetyl chloride (1.45 ml, 20,3 mmole, 10 eq.) in dry tetrahydrofuran (20 ml). The mixture was stirred at ~0° C. for six hours and extracted three times with ether. The combined organic extracts were washed with brine (30 ml), dried over anhydrous magnesium sulfate, filtered and evaporated to dryness to give 925.9 mg of the title G compound as an oil.

H. [1R-[1α,2β(4Z),3β,4α]]-N-[6-[3-[(Hexyloxy)methyl]-7-oxabicyclo[2.2.1]hept-2-yl]-4-hexenyl]-N-hydroxyacetamide A solution of the title G compound (500 mg, 1.11 mmole), in dry methanol (25 ml) was mixed with 98% pyridinium p-toluenesulfonate (467.1 mg, 1.29 mmole) and heated at 75° (oil bath) under nitrogen for 5 hours. The solvent was then evaporated in vacuo and the residual oil partitioned between water (25 ml) and ether (3×50 ml). The combined organic extracts were washed with brine (25 ml), dried over anhydrous magnesium sulfate, filtered and evaporated to dryness. The residual oil was chromatographed on a silica gel column to give 305.2 mg of the title compound as an oil.

EXAMPLE 3

1R-[1α,2β(5Z),3β,4α]-N-[7-[3-[(Hexyloxy)methyl]-7-oxabicyclo[2.2.1]hept-2-yl]-5-heptenyl]-N-hydroxyacetamide A. [1R-[1α,2β(Z),3β,4α]-7-[3-[(Hexyloxy)methyl]-7-oxabicyclo(2.2.1)hept-2-yl]-5-heptenoic acid, methyl ester A solution of [1R-[1α,2β(Z),3β,4α]-7-[3-[(Hexyloxy)-methyl]-7-oxabicyclo(2.2.1)hept-2-yl]-5-heptenoic acid (900 mg, 2.66 mmole) in dry ether (50 ml) was treated with an excess of diazomethane in ether and stirred at room temperature for one hour. The excess diazomethane was blown off with a stream of nitrogen and the colorless solution evaporated to dryness. The residual oil was chromatographed to give 1.1 g of the title A compound as an oil.

B. 1R-[1α,2β(Z),3β,4α]-7-[3-[(Hexyloxy)methyl]-7-oxabicyclo(2.2.1)hept-2-yl-5-heptenol A solution of the title A compound (2.1 g, 6.55 mmole) in dry tetrahydrofuran (10 ml) was added dropwise to a suspension of lithium aluminum hydride (410 mg, 10.8 mmole) in dry tetrahydrofuran (50 ml) under nitrogen at ~0° C. The mixture was stirred at 0° C. for 30 minutes and at room temperature for 2.5 hours, then quenched by the sequential addition of water (0.41 ml), 10% sodium hydroxide for 30 minutes, diluted with ether (200 ml) and filtered, washing the precipitates well with ether (50 ml). The filtrate was dried over anhydrous magnesium sulfate, filtered and evaporated to dryness to give 1.93 g of the title B compound as a homogeneous oil.

C. 1R-[1α,2β(Z),3β,4α]-7-[3-[(Hexyloxy)methyl]-7-oxabicyclo(2.2.1)hept-2-yl]-bromo-5-heptene A mixture of 99% triphenylphosphine (901 mg, 3.4 mmole), N-bromosuccinimide (611.7 g) and dry Celite (2.0 g) in a mixture of benzene (20 ml) and dry dichloromethane (5 ml) was stirred at 0° C. (ice bath) under nitrogen for 10 minutes and at room temperature for one hour. A solution of the title B compound (500 mg, 1.71 mmole) in dry dichloromethane (5 ml) was added to the complex and stirring continued at room temperature for 20 hours. The mixture was diluted with dichloromethane, stirred and filtered, washing the solids with more dichloromethane (50 ml). The organic extracts were evaporated to dryness and the residual oil partitioned twice between water (25 ml) and dichloromethane (25 ml). The organic phase was dried over anhydrous magnesium sulfate, filtered and evaporated to dryness to give an oil containing traces of starting material and triphenylphosphine. The crude product was chromatographed on a silica gel column to give the title C compound as a homogeneous oil (519 mg).

D. 1R-[1α,2β(Z),3β,4α]-7-[3-(Hexyloxy)methyl]-7-oxabicyclo(2.2.1)hept-2-yl]-N-[(tetrahydro-2-pyranyloxy)amino]-5-heptene A mixture of the title C compound (434.5 mg, 1.12 mmole), O-tetrahydropyranyloxy hydroxylamine (262.4 mg, 2.24 mmole) and sodium bicarbonate (940.8 mg, 11.2 mmole) in HMPA (5.4 ml) was heated at 60° under nitrogen for 12 hours. The reaction mixture was cooled, diluted with water (25 ml) and extracted twice with ether. The organic extracts were washed with water, dried over anhydrous magnesium sulfate, filtered and evaporated to dryness to give an oil which contained the desired compound as the major component and traces of the starting material and another product. This mixture was chromatographed on a silica gel column to give 432.5 mg of the title D compound as a homogeneous oil.

E. [1R-[1α,2β(Z),3β,4α]-N-[7-[3-[(Hexyloxy)-methyl]-7-oxabicyclo(2.2.1)hept-2-yl]-5-heptenyl]-N-(tetrahydro-2-pyranyloxy)-acetamide An emulsion of the title D compound (541 mg, 1.28 mmole) in 1N sodium hydroxide (28 ml) was stirred in an ice bath and was treated with acetyl chloride (0.91 ml, 12.8 mmole). The mixture was stirred at ~0° C. under nitrogen for another 2 hours, at room temperature overnight, and was extracted thrice with ether. The organic extracts were washed with brine (50 ml), dried over anhydrous magnesium sulfate, filtered and evaporated to dryness to give 510.5 mg of the title E compound as a homogeneous oil.

F. [1R-[1α,2β(5Z),3β,4α]-N-[7-[3-[(Hexyloxy)-methyl]-7-oxabicyclo[2.2.1]hept-2-yl]-5-heptenyl]-N-hydroxyacetamide A solution of the title E compound (510.5 mg, 1.1 mmole) in dry methanol (20 ml) was treated with 98% pyridinium p-toluenesulfonate (500 mg, 1.94 mmole) and heated under nitrogen at 55° for 35 hours. The solvent was evaporated in vacuo and the residual oil partitioned twice between methylene chloride (100 ml) and water (25 ml). The organic phase was washed with brine (25 ml) dried over anhydrous magnesium sulfate, filtered and evaporated to dryness to give a product mixture of the desired compound and starting material. This mixture was chromatographed on a silica gel column to give 217 mg of the title compound as an oil.

EXAMPLES 4 to 20

The following additional compounds within the scope of the present invention may be prepared by employing the teachings as outlined above and in the working Examples.

| Ex. No. | $R_1$ | $R_2$ | $R_3$ | A | n |
|---|---|---|---|---|---|
| 4 | —H | H | $CH_3$ | $-CH_2-CH=CH-$ | 2 |
| 5 | —H | $CH_3$ | $C_2H_5$ | $-CH_2-CH=CH-$ | 1 |
| 6 | $-C_2H_5$ | $CH_3$ | $C_5H_{11}$ | $-CH_2-CH=CH-$ | 3 |
| 7 | phenyl | H | $-CH=C(CH_3)_2$ | $-CH_2-CH=CH-$ | 3 |
| 8 | $-CH_2-$phenyl | H | $C_2H_5$ | — | 5 |
| 9 | $CH_2-CH_2-CH=CH-$ | $CH_3$ | $C_6H_{13}$ | $-CH_2-CH=CH-$ | 3 |
| 10 | $-CH_3$ | $-C(O)$phenyl | $CH_2-C\equiv C-CH_2-$ | $-CH_2-CH=CH-$ | 4 |
| 11 | $-C_3H_7$ | $-C(O)CH_3$ | $C_3H_7$ | — | 6 |
| 12 | $-CH_2-$phenyl | $-C(O)$phenyl | $CH_3$ | $-CH_2-CH=CH-$ | 2 |
| 13 | $-C_4H_9$ | H | $CH_2-CH=CH$ | — | 7 |
| 14 | phenyl | $-C(CH_2)_2CH_3$ with O | $CH_2-CH=CH-C_2H_5$ | $-CH_2-CH=CH-$ | 3 |
| 15 | $-CH_2-CH=CH-CH_3$ | H | $C_7H_{15}$ | $-CH_2-CH=CH-$ | 8 |
| 16 | $-CH_2-CH=CH-CH_3$ | $C_3H_7$ | $-CH_2-C\equiv C-CH_3$ | — | 9 |

-continued

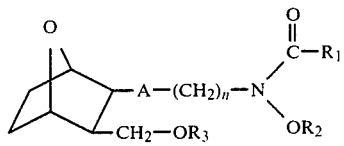

| Ex. No. | R₁ | R₂ | R₃ | A | n |
|---|---|---|---|---|---|
| 17 | −CH=C(CH₃)(CH₃) | C₄H₉ | CH₃ | −CH₂−CH=CH− | 4 |
| 18 | −CH=C(CH₃)(CH₃) | C₅H₁₁ | −CH=C(CH₃)(CH₃) | −CH₂−CH=CH− | 3 |
| 19 | −C₆H₅ (phenyl) | C₆H₁₃ | −CH=C(CH₃)(CH₃) | −CH₂−CH=CH− | 2 |
| 20 | −CH₂−CH=CHC₃H₇ | C₇H₁₅ | C₃H₇ | −CH₂−CH=CH− | 2 |

We claim:
1. A compound of the formula

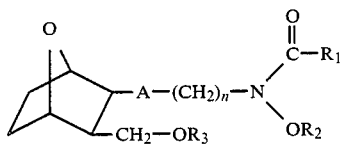

wherein $R_1$ is hydrogen, lower alkyl, aryl, aralkyl or alkenyl; $R_2$ is hydrogen, lower alkyl, alkanoyl or aroyl; $R_3$ is lower alkyl, alkenyl or alkynyl; A is −CH₂−CH=CH− or a single bond; and n is an integer from 0 to 9; with the proviso that when A is a single bond, n is an integer from 1 to 9, and including all stereoisomers and pharmaceutically acceptable salts thereof, and wherein alkyl or lower alkyl by itself or as part of another group comprises straight or branched chain radicals of up to 12 carbon atoms which may include a halo-substituent selected from fluorine, bromine, chlorine, iodine or CF₃, an alkoxy substituent, an aryl substituent, an aralkyl substituent, a haloaryl substituent, a cycloalkyl substituent, an alkylcycloalkyl substituent, hydroxy, an alkylamino or dialkylamino substituent, an alkanoylamino substituent, an arylcarbonylamino substituent, a nitro substituent, a cyano substituent, a thiol substituent or an alkylthio substituent;

wherein cycloalkyl, by itself or as part of another group, comprises saturated cyclic hydrocarbon groups having from 3 to 12 carbon atoms;

wherein aryl by itself or as part of another group is phenyl, naphthyl, substituted phenyl or substituted naphthyl wherein the substituent on either the phenyl or naphthyl may be 1 or 2 lower alkyl groups, 1 or 2 halogens selected from chlorine, fluorine or bromine, 1 or 2 lower alkoxy groups, 1 or 2 hydroxyl groups, 1 or 2 alkylamino or dialkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups;

wherein alkenyl comprises from 2 to 8 carbon atoms;
wherein alkynyl comprises from 3 to 8 carbon atoms;
wherein alkanoyl by itself or as part of another group comprises an alkyl carbonyl group of up to 12 carbon atoms or an alkenyl carbonyl group of from 3 to 8 carbon atoms; and,
wherein aroyl by itself or as part of another group comprises an aryl carbonyl group.

2. A compound of claim 1 wherein $R_1$ is alkyl, $R_2$ is hydrogen, $R_3$ is alkyl, A is −CH₂−CH=CH− and n=2.

3. A compound of claim 1 wherein $R_1$ is alkyl, $R_2$ is hydrogen, $R_3$ is alkyl, A is −CH₂−CH=CH− and n=3.

4. A compound of claim 1 wherein $R_1$ is alkyl, $R_2$ is hydrogen, $R_3$ is alkyl, A is −CH₂−CH=CH− and n=4.

5. A compound of claim 1 having the name [1R-[1α,2β(3Z),3β,4α]]-N-[5-[3-[(Hexyloxy)-methyl]-7-oxabicyclo[2.2.1]hept-2-yl]-3-pentenyl]-N-hydroxyacetamide.

6. A compound of claim 1 having the name [1R-[1α,2β(4Z),3β,4α]]-N-[6-[3-[(Hexyloxy)-methyl]-7-oxabicyclo[2.2.1]hept-2-yl]-4-hexenyl]-N-hydroxyacetamide.

7. A compound of claim 1 having the name 1R-[1α,2β(5Z),3β,4α]-N-[7-[3-[(Hexyloxy)-methyl]-7-oxabicyclo[2.2.1]hept-2-yl]-5-heptenyl]-N-hydroxyacetamide.

8. A composition for inhibiting allergic conditions in a mammalian species comprising an effective amount of a compound as defined in claim 1 or a pharmaceutically acceptable salt thereof and a pharmaceutically acceptable carrier therefor.

9. A method of simultaneously inhibiting arachidonic acid cyclooxygenase and arachidonic acid 5-lipoxygenase which comprises administering to the circulatory system of a mammalian host an effective amount of a compound as defined in claim 1 or a pharmaceutically acceptable salt thereof.

10. The method of claim 9 wherein said compound is administered in an amount within the range of from about 1 to about 100 mg/kg.

11. A method for treating asthma in a mammalian species in need of such treatment, which comprises administering to a mammalian host an effective amount of a compound as defined in claim 1 or a pharmaceutically acceptable salt thereof.

12. A method of treating psoriasis in a mammalian species in need of such treatment which comprises administering to a mammalian host an effective amount of a compound as defined in claim 1 or a pharmaceutically acceptable salt thereof.

* * * * *